United States Patent [19]

Mochida et al.

[11] 4,200,436
[45] Apr. 29, 1980

[54] IMMUNOCHEMICAL MEASURING PROCESS

[75] Inventors: Ei Mochida, Tokyo; Nobuhisa Ogawa, Omiya; Hiroyuki Shinkai, Kawagoe; Masakatsu Hashimoto, Tokyo, all of Japan

[73] Assignee: Mochida Seiyaku Kabushiki Kaisha, Tokyo, Japan

[21] Appl. No.: 837,434

[22] Filed: Sep. 28, 1977

[30] Foreign Application Priority Data

Sep. 30, 1976 [JP] Japan ................ 51-117621

[51] Int. Cl.$^2$ ............................................. G01N 33/16
[52] U.S. Cl. ................................. 23/230 B; 23/230.6;
23/915; 23/920; 435/7; 424/1; 424/8; 424/12
[58] Field of Search .................. 23/230 B; 424/1, 12, 424/8; 252/408; 195/103.5 A

[56] References Cited

U.S. PATENT DOCUMENTS

| 3,654,090 | 4/1972 | Schuurs | 195/103.5 A |
|---|---|---|---|
| 3,992,516 | 11/1976 | Lim | 424/12 X |
| 4,002,532 | 1/1977 | Weltman | 424/12 X |
| 4,067,959 | 1/1978 | Bolz | 424/12 |

OTHER PUBLICATIONS

"Immunoenzymatic Techniques", G. Feldmann et al., eds. chapter by M. F. Gourdin et al., 245–253, North-Holland Publishing Co., New York, 1976.
E. A. Kabat, "Structural Concepts in Immunology and Immunochemistry", 162–167, Holt, Rinehart & Winston, Inc., New York, 1968.

*Primary Examiner*—Sidney Marantz
*Attorney, Agent, or Firm*—Brisebois & Kruger

[57] ABSTRACT

Immunochemical process of measuring antigenic substances such as human chorionic gonadotropin, growth hormone, insulin, immunoglobulins using a labeled antibody, which makes a monovalent bond to the antigen, and insolubilized antigen.

The labeled monovalent antibody used is a monovalent antibody obtained by digesting the antibody to an antigen to be measured with papain according to Porter's method or by reducing a fragment obtained by digesting the antibody with pepsin according to Peterman's method.

7 Claims, 5 Drawing Figures

IMMUNOCHEMICAL MEASURING PROCESS

BACKGROUND OF THE INVENTION

Taking advantage of excellent specificity and sensitivity of the reaction of antigenic substances such as human chorionic gonadotropin, growth hormone, insulin and immunoglobulins to bind to their antibodies, numerous attempts have been made to measure such antigenic substances and their antibodies and already many immunochemical measuring processes are in practical use.

For instance there are available the following processes: immunodifusion methods, in which the antigen and the antibody are reacted together in agar gel; agglutination reactions and agglutination inhibition reactions, in which blood cells or fine particles of polystyrene latex are employed as carriers of an antigen or antibody; radioimmunoassay (RIA), in which radioisotopes are employed as a labeling agent; enzyme immunoassay (EIA), in which enzymes are used to label the antigen or the antibody; and fluorescence immunoassay, in which fluorescent substances are used to label the antigen or antibody.

Meanwhile, for the purpose of measuring low molecular weight substances such as steroids, thyroid hormones, physiologically active peptides or amines, whose antibodies are difficult to produce, a competitive protein binding assay which utilizes the reaction with a receptor protein or binding protein, i.e., protein which specifically binds to such low molecular weight substances, has been employed. Recently, however, these substances have come to be measured by the same processes as applied to the above-mentioned antigenic high molecular substances, because the antibodies of even these low molecular weight substances are now relatively easy to produce.

These processes have respective characters and are found widely applicable. Among others, RIA and EIA, which highly excel in the sensitivity of measurement and quantitative precision, are widely used, the substances measurable by them including a great variety of high molecular substances such as protein hormones, immunoglobulins, virus and low molecular weight ones such as peptides, steroids, amines, synthetic medicines.

The principle is common to RIA and EIA; use of a labeled antigen in which the antigen is labeled by a labeling agent or use of a labeled antibody in which the antibody is labeled by a labeling agent.

The process utilizing a labeled antigen is a so-called competitive process in which an unknown amount of unlabeled antigen and a given amount of labeled antigen are made to react competitively with a given amount of an antibody, whereby the activities of the labeling agent which is bound to an antibody or the labeled antigen which is not bound to it are measured. In the meantime, a dilution series of a reference substance, whose concentration is known, is prepared and in the same way described above the activity of the labeling agent in each dilution is measured. A standard curve obtained by plotting the measured activities is used to determine the amount of the substance to be measured. As a means to separate the labeled antigen which is bound to the antibody and the one which is not, an insolubilized antibody is employed.

In the process after reaction between an unknown amount of antigen and a given amount of labeled antibody the activities of the labeled antibody which is bound to the antigen or the labeled antibody which is not bound to it are measured. In the meantime, a dilution series of reference substance, whose concentration is known, is prepared and in the same way described above the activity of labeling agent in each dilution is measured. A standard curve obtained by plotting the measured activities is utilized for determining the amount of the substance to be measured. As a means to separate the labeled antibody which is bound to the antigen and the one which is not, an insolubilized antigen or an insolubilized antibody is employed.

The process employing the insolubilized antibody is a so-called sandwich process, which highly excels in the sensitivity of measurement. Its advantages are, however, detracted by the disadvantages that an antibody with fewer binding sites than an antigen is made insoluble for the purpose, the reactivity with the antigen to be measured decreases; and the process is not available for measurement of haptens.

By contrast the process employing the insolubilized antigen, which suffers less decrease in reactivity due to the antigen being rendered insoluble, can measure haptens but it is low in the sensitivity of measurement for reasons stated later.

SUMMARY OF THE INVENTION

The primary object of present invention is to provide an immunochemical process for measuring physiologically active substances.

Another object of the present invention is to provide process for measuring with high precision and sensitivity physiologically active substances.

Another object of the present invention is to provide the reagents for measuring physiologically active substances according to the principle based on the said process.

REFERENCE TO DRAWINGS

DETAILED DESCRIPTION OF THE INVENTION

The present invention concerns an improvement of the process using a labeled antibody and insolubilized antigen (to be referred to hereafter as inhibition process), in which an antibody which makes a monovalent bond to the antigen is used as the antibody to be labeled.

The principle of the present invention as compared with the inhibition process is described below referring to the drawings.

Figure 1:
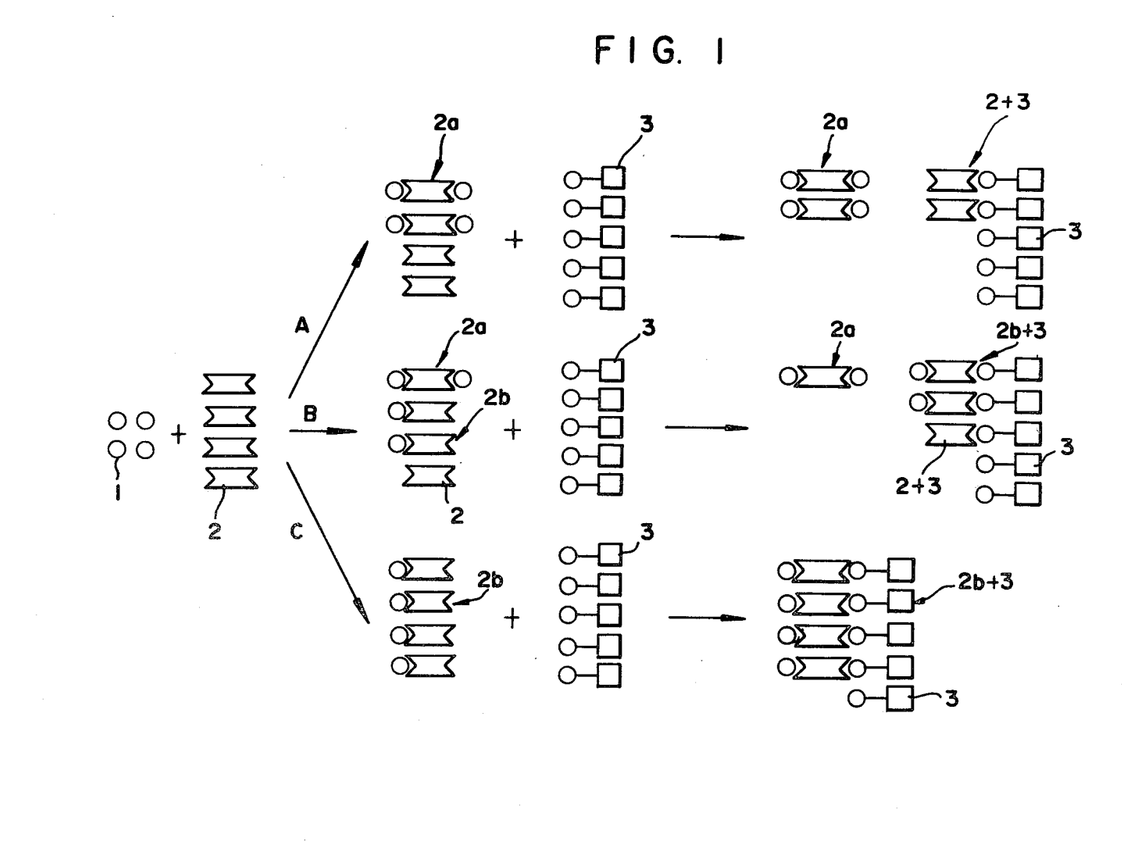
FIG. 1 is a diagram showing a measurement by the conventional inhibition process.

According to the conventional inhibition process, as illustrated in FIG. 1, the antigen to be measured (hereafter referred to as the ANTIGEN) 1 is reacted with a given amount of the labeled antibody 2, i.e., an antibody to this ANTIGEN which has been labeled, thereby producing a labeled antibody-ANTIGEN complex 2a. To the reacted solution is added an insolubilized antigen 3. Thereupon, as shown in FIG. 1-A, the labeled antibody 2 which has not bound to the ANTIGEN binds to the insolubilized antigen 3. Thus the labeled antibody-ANTIGEN complex 2a which is bound to the ANTIGEN, and the labeled antibody-insolubilized antigen complex 2+3 which is not bound to the ANTIGEN can be separated from each other. The reaction mechanism is thereby supposed to be as follows: The labeled antibody 2, all of which ought to bind to the insolubilized antigen 3 in the absence of the ANTIGEN 1, has been prevented from binding to it by the presence of ANTIGEN 1.

Since the labeled antibody 2 usually makes a divalent bond, the ANTIGEN 1—if it is small in amount—binds at one of the two active sites of the antibody 2, thus producing an unsaturated complex 2b as illustrated in FIG. 1-B and 1-C. This unsaturated complex 2b, upon addition of the insolubilized antigen 3, binds to the insolubilized antigen 3 at a free active site thereby yielding 2b+3. Thus it is impossible to clearly separate the labeled antibody 2a which is bound to the ANTIGEN from the labeled antibody 2+3 which is not bound. Therefore, the precision and sensitivity of measurement become low.

If, as illustrated in FIG. 1-C, the ANTIGEN 1 binds to all the labeled antibody 2 solely at one active site to yield a complex 2b, the binding of the labeled antibody 2 to the insolubilized antigen 3 is not prevented and accordingly with a change in the amount of the ANTIGEN 1 not reflected by a change in the activity of the labeled antibody, the sensitivity of measurement is lower.

Figure 2:
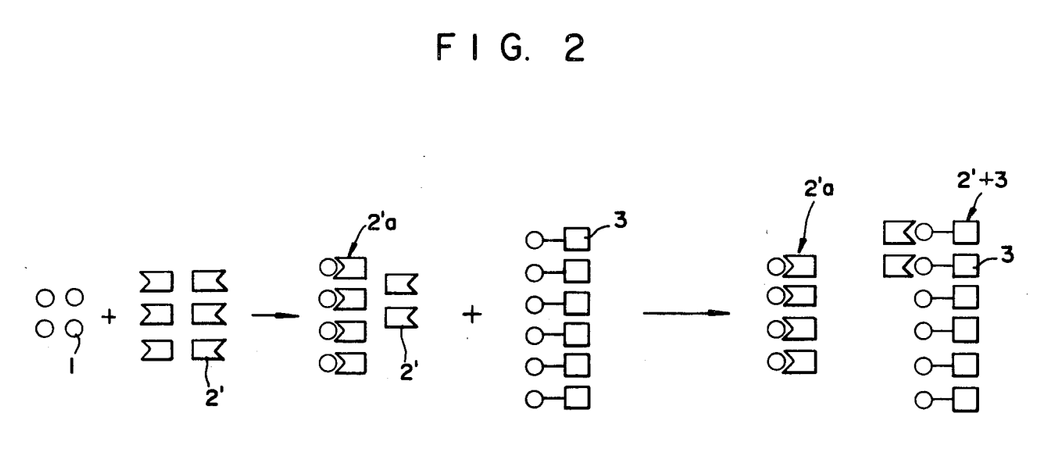
FIG. 2 is a diagram showing an immunochemical measuring process according to the present invention.

According to the present invention utilizing a labeled antibody which makes a monovalent bond to the antigen, as illustrated in FIG. 2 the active site of the antibody 2' is single; accordingly the antibody 2'a which is bound to the ANTIGEN 1 can no longer bind to the insolubilized antigen 3; and thus the preventive effect of the ANTIGEN 1 being perfect, clear separation can be made between the labeled antibody 2'a which is bound to the ANTIGEN and the labeled antibody 2' which is not bound, resulting in a very precise measurement. Moreover the present invention gives an improved precision of measurement, because a change in the amount of the ANTIGEN—even if it is very small—can be directly measured in terms of a change in the amount of the labeled antibody which is bound to the ANTIGEN or of the one which is not bound to it.

The present invention is usually executed as follows.

An adequately diluted test sample is added to a solution of a labeled monovalent antibody and the reaction mixture is incubated. To the mixture is added a suspension of the insolubilized antigen. After incubation, the mixture is centrifuged to separate the solid phase from the liquid phase; and then the activity of the labeled antibody contained in the solid phase or the liquid phase is measured. If the labeling agent is, for instance an enzyme, the separated solid or liquid phase is added to an appropriate substrate solution to react; the activity of the enzyme is measured; and the amount of the test object contained in the test sample is determined by plotting the measured activity on a standard curve prepared in the same performance using a reference substance whose concentration is known.

For execution of measurement the conditions of measurement such as the volume of the test sample, the concentration and volume of the reagents and the reaction time should be experimentally selected depending on the kind of substance to be measured, the titer of the antibody to be used and the kind and specific activity of the labeling agent.

As the monovalent antibody to be used in the present invention, the following are recommendable: a fragment (to be called Fab) of an antibody to the ANTIGEN digested with papain by Porter's method (Porter, R.R., Biochem. J. 73, 119 (1959)); and a fragment of it digested with pepsin by Peterman's method (Peterman, M.L., J. Phys. Chem., 45, 1 (1941)) and reduced to a monovalent antibody. (The fragment obtained is called Fab'.)

To separate the labeled monovalent antibody which has bound to the ANTIGEN from the labeled antibody which has not bound to it, use of an insolubilized antigen is recommendable.

For the purpose of rendering the antigen insoluble, the prior art processes may be used such as using polysaccharides (for instance, cellulose, agarose, dextran) or plastics (for instance, polystyrene, polyethylene, polypropylene, polyvinylchloride, polyacetal, acrylonitrile-butadiene-styrene copolymer) as the carrier, and chemically binding or physically adsorbing it.

As the labeling agents for the antibody one may: radioisotopes (for instance, $^{125}I$, $^{131}I$, $^{3}H$, $^{14}C$), enzymes (for instance, horseradish peroxidase, alkaline phosphatase, $\beta$-D-galactosidase, glucose oxidase, glucoamylase) and fluorescent materials (for instance, fluorescein isothiocyanate, rhodamine); but when the sensitivity, the precision and the convenience of measurement are taken into consideration, use of an enzyme would be advantageous.

These labeling agents can be made to bind to the antibody by known means such as Hunter-Greenwood's method (Hunter, W.M., Greenwood,..., Nature, 194, 495 (1962)) or P. Nakane-A. Kawaoi's method (P. Nakane, A. Kawaoi, J. Hisochem. Cytchem., 22, 1084 (1974)).

The antigens measurable by the present invention include high molecular substances, i.e., the so-called complete antigens, for instance, human chorionic gonadotropin, growth hormone, insulin, adrenocorticotropic hormone, thyroid stimulating hormone, immunoglobulin E, $\alpha$-fetoprotein, hepatitis B antigen, human placental lactogene; and low molecular ones, i.e., the so-called haptens, for instance, steroids such as testosterone, estriol, progesterone, corticosterone, aldosterone; thyroid hormones such as thyroxine, triidothyronin; peptides such as bradykinin, angiotensin, thyroid hormone-releasing hormone, luteinizing hormone-releasing hormone; physiologically active amines such as epinephrine, norepinephrine, histamine, serotonin; prostaglandin. For measurement of haptens, use of hapten-protein conjugate which have been insolubilized would be advantageous.

The present invention improves the low sensitivity and the lower precision of measurement in the conventional inhibition process through use of a labeled monovalent antibody and this is an important matter particularly in the measurement of haptens. Since haptens make a monovalent bond with the antibody, the sandwich process cannot be applied and thus the competitive process or inhibition process has to be used. Both of these processes are low in the sensitivity of measurement, but using the invented process, not only complete antigens but also haptens can be measured with satisfactory sensitivity and precision.

In the following table are compared the sensitivity of measurement of different processes using an enzyme as the labeling agent in the measurement of the human chorionic gonadotropin and estriol. It is evident from this table that the invented process is far superior in the sensitivity of measurement to the conventional inhibition process.

Table

|  |  | Human chorionic gonadotropin (complete antigen) (mIU/ml) | Estriol (hapten) (ng/ml) |
|---|---|---|---|
| Invented process | | 0.1–1.0 | 0.2 |
| Conventional | Inhibition process | 5–20 | 0.5 |
| | Competitive process | 10–20 | 3.0 |
| | Sandwich process | 0.1–1.0 | — |

The following examples illustrate the present invention.

Example 1—Measurement of human chorionic gonadotropin (hCG)

(a) Preparation of standard solutions of hCG

The standard hCG mentioned in Japanese Pharmacopoeia was dissolved in a phosphate buffered saline (PBS) containing 0.1% bovine serum albumin (BSA) to yield solutions with concentrations 500, 50, 5 and 0 IU/l.

(b) Preparation of anti-hCG antibody

A rabbit was routinely immunized against hCG and therefrom an anti-hCG serum was obtained. By salting out the obtained serum with sodium sulfate, an anti-hCG antibody globulin was produced.

(c) Preparation of anti-hCG antibody Fab

The anti-hCG antibody produced in (b) ws papain-digested by Porter's method and fractionated with the carboxymethyl cellulose column (pH 5.5), thereby producing the anti-hCG antibody Fab.

(d) Preparation of an anti-hCG antibody Fab-enzyme conjugate

Five mg of horseradish peroxidase (HRP) was dissolved in 1 ml of 0.3 M freshly made sodium bicarbonate (pH 8.1); after adding 0.1 ml of 1% 2,4- dinitrofluorobenzene in absolute ethanol; the mixture was stirred for one hour at room temperature. This was followed by addition of 1 ml of 0.08 M sodium periodate in distilled water, mixing for 30 minutes at room temperature, addition of 1.0 ml of 0.16 M ethylenglycol in distilled water and then mixing for one hour at room temperature. After dialysis overnight against 0.01 M sodium carbonate buffer (pH 9.5), 1.0 ml of a solution of the above-mentioned anti-hCG antibody Fab fragment dissolved in 0.01 M sodium carbonate buffer (pH 9.5) to a concentration of 5 mg/ml was added and was stirred for 3 hours at room temperature. This was followed by addition of 5 mg of sodium borohydride and then by reaction for 3 more hours at 4° C. The mixture was dialyzed overnight against PBS (pH 7.2), then was applied to a Sephadex G-200 (Pharmacia Finechemical) column. Thus, purified anti-hCG antibody Fab-HRP conjugate was obtained.

(e) Preparation of hCG coupled cellulose

Eight g of cellulose powder was added to 320 ml of 2.5% cyanogen bromide. The suspension obtained was adjusted to pH 10–11 by means of 1 N sodium hydroxide. After reaction for 2 minutes under stirring, it was passed through a glass filter, washed with 0.1 M sodium bicarbonate, producing activated cellulose. After the obtained active cellulose was suspended in 32 ml of 0.1 M sodium bicarbonate; 8 mg of hCG was added; reacted under stirring for 22 hours at 4° C.; and then washed with PBS and suspended in PBS containing 1% BSA.

(f) Measurement of hCG

Figure 3:
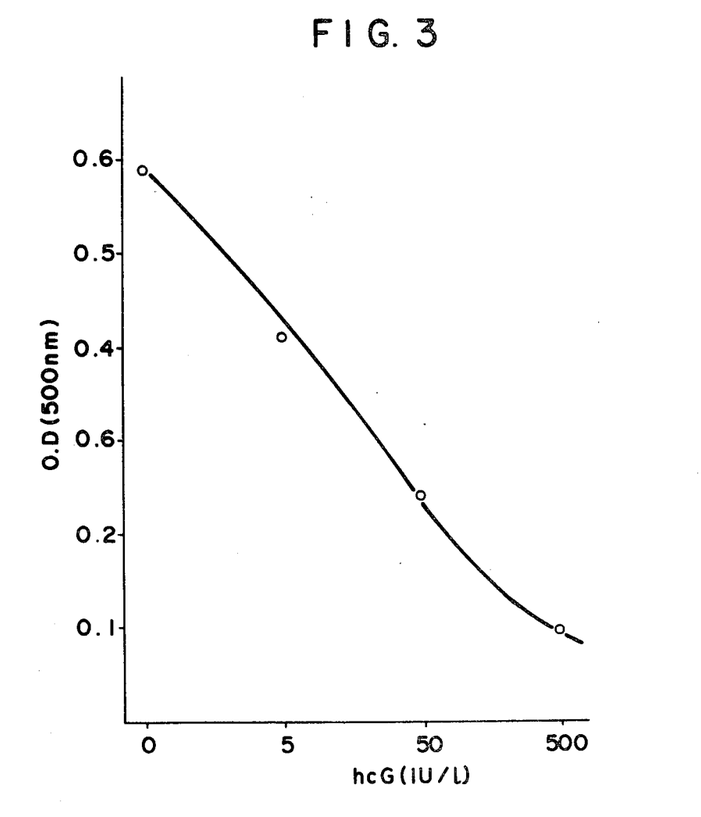
FIG. 3 graphically shows the measured results in Example 1 according to the present invention.

One tenth ml of each standard hCG solution, 0.1 ml of anti-hCG antibody Fab-HRP conjugate solution in (d) and 0.3 ml of PBS containing 0.5% BSA and 0.5% Tween 20 (Atlas Powder), which had been added into a test tube, were incubated for one hour at room temperature. This was followed by addition of 0.3 ml of hCG coupled cellulose suspension obtained in (e) and then by incubation for 2 hours at room temperature. After the incubation the solid phase was washed with a physiological saline containing 0.005% Tween 20, 3 ml of substrate solution (5-aminosalicylic acid 60 mg/dl, 0.3% hydrogen peroxide 1 ml/dl) was added to the solid phase, then the mixture was allowed to stand for 60 minutes at room temperature. The reaction was stopped by addition of one drop of 1.6% sodium azide, followed by centrifugation. Then the absorbance of the supernatant fluid at 500 nm was measured, the results are illustrated in FIG. 3.

Example 2—Measurement of estriol (a) Preparation of standard estriol solution

Estriol (Sigma Chemical) was dissolved in PBS (pH 6.4) containing 0.1% BSA to concentrations of 160, 40, 10, 2.5 and 0 ng/ml.

(b) Preparation of estriol-16,17-dihemisuccinate-BSA conjugate

Six hundreds mg of estriol-16,17-dihemisuccinate (Am. J. Obest. Gyn., 109, 897 (1971)) was dissolved in 12 ml of dioxane and thereto was added 0.3 ml of tri-n-butylamine. Then at 12° C., 0.17 ml of isobutyl chlorocarbonate was added and the solution was mixed well by stirring. The solution was mixed with a solution obtained by dissolving BSA 1.7 g in 40 ml of distilled water, adjusted to pH 12.0 by 1 N sodium hydroxide and thereto was added 40 ml of dioxane and kept at 12° C. After reaction for 4 hours under stirring, unreacted low molecular substances were separated by means of Sephadex G-25 column. This was followed by dialysis against 0.1% sodium azide solution and lyophilizing, thereby producing estriol-16, 17-dihemisuccinate-BSA conjugate.

(c) Preparation of estron-17-oxime-haemoglobin conjugate

Six hundreds and eighty-seven mg of estron-17-oxime (Erlanger, B. F., J. Biol. Chem., 234, 1090 (1959)) was dissolved in 20 ml of dioxane. After addition of 0.9 ml of tri-n-butyl-amine, the solution was kept at 11° C. and followed by stirring and adding of 0.27 ml of isobutyl chlorocarbonate. The solution was mixed with a solution obtained by dissolving 2.42 g of haemoglobin (Hb) in 70 ml of distilled water, adjusted to pH 9.5, further mixed with 70 ml of dioxane and kept at 11° C. This was followed by reaction for 4 hours under stirring and then by separation of unreacted low molecular substances with a column chromatography using Sephadex G-25. The substances thus obtained were dialyzed against 0.1% sodium azide and lyophilized, thereby producing an estron-17-oxime-Hb conjugate.

(d) Preparation of anti-estriol antibody

The estriol-16,17-dihemisuccinate-BSA conjugate obtained in (b) was dissolved in physiological saline. Together with Freund's complete adjuvant, the emulsion was subcutaneously injected into an adult rabbit's back repeatedly, 2 mg of the conjugate each time. After a rise in the antibody titer was confirmed, the blood was collected; serum was separated and salted out with sodium sulfate, thereby yielding a globulin fraction. Then the antibody to BSA was removed from this antibody with use of BSA coupled Sepharose (Pharmacia Finechemical). The BSA coupled Sepharose was added at a rate of 25 ml to 50 ml of the antibody solution. Left at 37° C. for 30 minutes, the suspension was incubated overnight at 4° C. The liquid phase was separated therefrom by centrifugation for 10 minutes at 4° C., thereby producing an antibody specific to estriol.

(e) Preparation of anti-estriol antibody Fab-HRP conjugate

By treating the antibody obtained in (d) in the same way as in Example 1(-c), and anti-estriol antibody Fab fragment was obtained. The Fab and HRP were reacted together in the same way as in Example 1(-d), thereby yielding an anti-estriol antibody Fab-HRP conjugate.

(f) Preparation of estron-17-oxime-haemoglobin coupled cellulose

Using 8 mg of estron-17-oxime-haemoglobin, estron-17-oxime-haemoglobin coupled cellulose was obtained by the process described in Example 1(-e).

(g) Measurement of estriol

Figure 4:
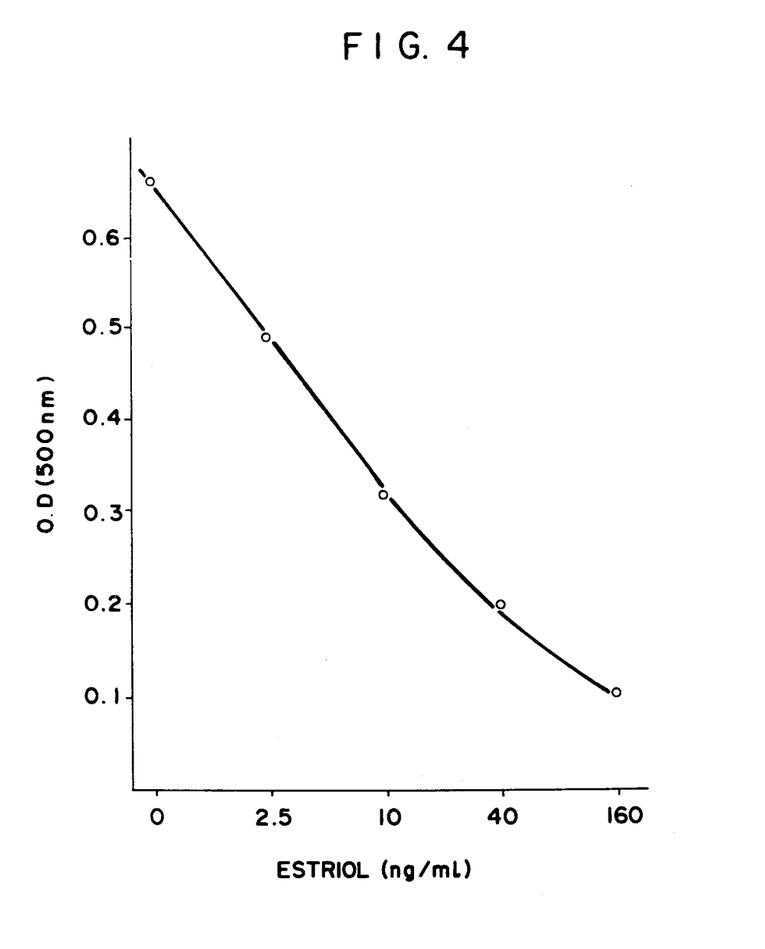
FIG. 4 graphically shows the measured results in Example 2 according to the present invention.

One tenth ml of each standard estriol solutions in (a), 0.1 ml of anti-estriol antibody Fab-HRP conjugate solution in (e) 0.3 ml of PBS containing 0.5% BSA and 0.5% Tween 20 were added to a test tube and the mixture was incubated for one hour at room temperature. To the solution was added 0.3 ml of estron-17-oxime-haemoglobin coupled cellulose suspension in (f) and it was incubated for 2 hours at room temperature. Thereafter in the same way as in Example 1, the absorbance at 500 nm was measured, the results being illustrated in FIG. 4.

Example 3—Measurement of insulin (a) Preparation of standard insulin solution

Bovine crystal insulin (Sigma Chemical. 25 IU/mg) was dissolved in PBS containing 0.1% BSA to concentrations of 160, 80, 40, 20, 10, 5 and 0 μIU/ml.

(b) Preparation of anti-insulin antibody

Bovine crystal insulin was suspended in physiological saline; thereafter dissolved by adding 0.1 N hydrochloric acid drop by drop and adjusted to a concentration of 2 mg/ml. The insulin solution was mixed with activated charcoal powder (Wako Pure Chemical) at a rate of 10 mg to 1 ml of said insulin solution, thereby causing insulin to be adsorbed on activated charcoal. The activated charcoal being adsorbed insulin thereon was centrifugally separated. By adding 0.5 ml of physiological saline to 10 mg of this activated charcoal, an insulin adsorbed activated charcoal suspension was obtained.

A guinea pig was injected every other week a mixture of 0.25 ml of this suspension and 0.25 ml of Freund's complete adjuvant and the injection was repeated 10 times. One week after the final injection, the blood was collected from the animal's carotid, thereby producing a guinea pig anti-insulin serum. The antiserum thus obtained was salted out two times with sodium sulfate and the anti-insulin antibody was obtained.

(c) Labeling of anti-insulin antibody Fab with $^{131}I$

The anti-insulin antibody produced in (b) was treated in the same way as in Example 1(-c), thereby producing the anti-insulin antibody Fab. Using Hunter-Greenwood's method, this Fab was labeled with $^{131}I$.

In a small test tube, 2 mCi of Na $^{131}I$ (0.005 ml) was added to 0.0025 ml of 0.5 M phosphate buffer, and then 0.0025 ml of Fab solution and 0.02ml of chloramin T were added and mixed. Ten seconds later, the reaction was stopped by addition of 0.1 ml of sodium pyrosulfite. After fractionation by a column chromatography of Sephadex G-25, $^{131}I$-anti-insulin antibody Fab was obtained.

(d) Preparation of insulin coupled Sepharose

Ten ml of Sepharose was washed with distilled water on a glass filter and then suspended in 20 ml of distilled water. The suspension was mixed with 20 ml of 2.5% cyanogen bromide; adjusted to pH 10–11 with 1 N sodium hydroxide and caused to react for 8 minutes. Then it was passed through a glass filter and washed with distilled water and followed by washing with 0.1 M sodium bicarbonate, then suspended in 10 ml of insulin solution (50 mg/10 ml) and caused to react at 4° C. overnight. After the reaction, it was well washed with physiological saline and suspended in PBS containing 0.5% BSA.

(e) Measurement of insulin

One tenth ml of each standard insulin solution in (a), 0.1 ml of $^{131}I$-anti-insulin antibody Fab solution in (c) and 0.3 ml of PBS containing 0.5% BSA and 0.5% Tween 20 were added to a counting test tube and allowed to stand for one hour at room temperature. Then 0.2 ml of insulin coupled Sepharose suspension in (d) was added thereto and was incubated for 2 hours at room temperature. After washing two times with physiological saline containing 0.005% Tween 20, the radioactivity of the sediments was measured. By this process, more than 0.1 μIU of insulin can be measured.

Example 4—Measurement of α-fetoprotein (a) Preparation of standard α-fetoprotein solution α-fetroprotein (AFP) extracted from abdominal ascites of patient's with primary hepatoma and purified by S. Nishi and other's method (Cancer Res., 30, 2507 (1970)) was dissolved in PBS containing 0.5% BSA and 0.5% Tween 20 to concentrations of 160, 80, 40, 20, 10 and 5 ng/ml.

(b) Preparation of anti-AFP antibody

Purified AFP was dissolved to a concentration of 2 mg/ml in physiological saline and 0.5 ml of the solution was mixed with 0.5 ml of Freund's complete adjuvant. A rabbit was injected more than 5 times with the mixture for immunization, thereby producing the anti-AFP serum. By salting out with sodium sulfate the anti-AFP antibody was obtained from this antiserum.

(c) Preparation of anti-AFP antibody Fab

In the same way as in Example 1(-c) the anti-AFP antibody in (b) was submitted to papain-digestion, thereby producing the anti-AFP antibody Fab fragment.

(d) Preparation of anti-AFP antibody Fab-enzyme conjugate

Three tenth ml of alkaline phosphatase (Grade 1) (boehringer mannheim) solution (5 mg/ml) was centrifuged and, after the supernatant fluid was removed, it was dissolved in 0.1 ml of the anti-AFP antibody Fab in (c). After dialysis overnight against PBS, it was mixed with 0.01 ml of 4.2% glutaraldehyde and the mixture was incubated for 2 hours at room temperature. Then, the volume of the solution was adjusted to 1 ml with addition of PBS. Dialysis overnight against PBS the dialysate was fractionated by a Sepharose 6B column chromatography, thereby yielding an anti-AFP antibody Fab-alkaline phoshatase conjugate.

(e) Preparation of AFP coupled cellulose

In accordance with the process in Example 1(-e), 8 g of cyanogen bromide-activated cellulose and 8 mg of AFP were reacted together, producing an AFP coupled cellulose.

(f) Measurement of AFP

Figure 5:
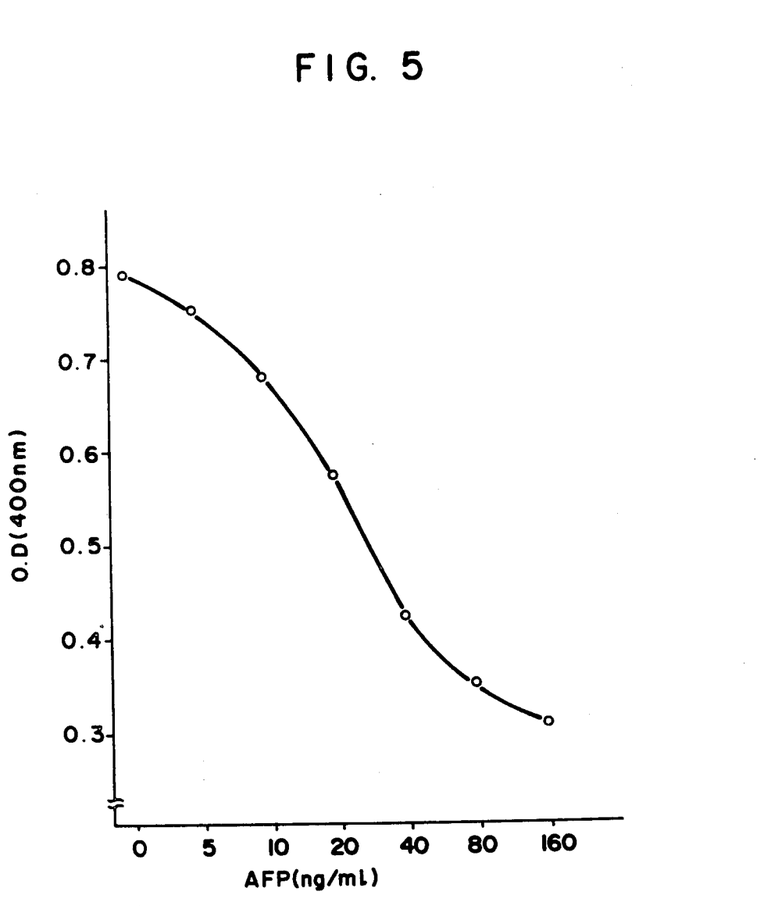
FIG. 5 graphically shows the measured results in Example 3 according to the present invention.

One tenth ml of standard AFP solution in (a) and 0.1 ml of anti-AFP antibody Fab-alkaline phosphatase conjugate solution in (e) were put in a test tube, the suspension was incubated for 2 hours at room temperature. Next, the solid phase in the suspension was washed with physiological saline containing 0.005% Tween 20 and thereto was added 3 ml of a substrate solution (P-nitrophenylphosphate 100 mg/dl, magnesium chloride 1 mM, pH 9.8), followed by standing for one hour at room temperature. Then by addition of 0.3 ml of 1 N sodium hydroxide the reaction was stopped and after centrifugation the absorbance of the supernatant was measured, the results are shown in FIG. 5.

What is claimed is:

1. Immunochemical measuring process comprising the steps of
   (a) reacting an antigen to be measured with labeled monovalent antibody obtained by bonding a labeling agent to an antibody which makes a monovalent bond to the antigen,
   (b) reacting insolubilized antigen obtained by insolubilizing the same antigen as that to be measured, with the reaction mixture produced in step (a),
   (c) separating the reaction mixture of step (b) into a solid phase and a liquid phase, and
   (d) measuring the activity of the labeling agent of the solid phase or liquid phase separated in step (c).

2. The immunochemical measuring process of claim 1, wherein the monovalent antibody is a papain-digested fragment of the antibody to the antigenic substance to be measured or a pepsin-digested and reduced fragment of the antibody to the antigenic substance to be measured.

3. The immunochemical measuring process of claim 1, wherein the labeling agent is a radioisotope, enzyme or a fluorescent material.

4. The immunochemical measuring process of claim 1, wherein the antigenic substance to be measured is a complete antigen or a hapten.

5. The immunochemical measuring process of claim 1, in which the labeled antibody and the insolubilized antigen are lyophilized.

6. The immunochemical measuring process of claim 1, wherein the insolubilized antibody is an antigen insolubilized by binding to a carrier.

7. The immunochemical measuring process of claim 4, wherein the carrier is polysaccharide or plastic.

* * * * *